United States Patent [19]

Stödberg et al.

[11] 4,128,767

[45] Dec. 5, 1978

[54] X-RAY PRIMARY RADIATION DIAPHRAGM ASSEMBLY

[75] Inventors: Lars Stödberg, Stenhamra; Hans Sjöström, Spanga, both of Sweden

[73] Assignee: Siemens Aktiengesellschaft, Berlin & Munich, Fed. Rep. of Germany

[21] Appl. No.: 794,406

[22] Filed: May 6, 1977

[30] Foreign Application Priority Data

Jul. 22, 1976 [DE] Fed. Rep. of Germany ....... 2633059

[51] Int. Cl.² ................................................. A61B 6/06
[52] U.S. Cl. ..................................................... 250/513
[58] Field of Search ......................................... 250/513

[56] References Cited

U.S. PATENT DOCUMENTS 2,667,588  1/1954  Oswald ................................. 250/513

Primary Examiner—Alfred E. Smith
Assistant Examiner—T. N. Grigsby
Attorney, Agent, or Firm—Hill, Gross, Simpson, Van Santen, Steadman, Chiara & Simpson

[57] ABSTRACT

In the illustrated embodiment sets of four diaphragm plates are utilized to define the margins of a beam path configuration having the shape of a four-sided pyramid with its vertex coinciding with the focus of the x-ray tube. Each set of four diaphragm plates is mounted by means of levers which are capable of being pivoted in a scissors-like fashion so as to adjust the angle of divergence of the x-ray beam with respect to a given plane. For actuating the levers, a motor driven cam is coupled with the levers via a roller and a pair of links, a tension spring urging the levers in a direction so as to press the roller into following relation to the cam surface.

3 Claims, 2 Drawing Figures

X-RAY PRIMARY RADIATION DIAPHRAGM ASSEMBLY

BACKGROUND OF THE INVENTION

The invention relates to an x-ray primary radiation diaphragm assembly comprising two pairs of diaphragm plates staggered 90° which, when said diaphragm is mounted in operative relation to an x-ray tube housing, are disposed close-to-focus, and comprising two pairs of diaphragm plates, likewise staggered 90°, which, when said diaphragm is mounted, are disposed remote-from-focus, and wherein the plates of each pair of diaphragm plates are commonly adjustable symmetrically relative to the longitudinal axis of the diaphragm assembly such that the diaphragmed beam path configuration has the shape of a pyramid with its vertex lying at the focus of the x-ray tube (when said diaphragm assembly is mounted in operative relation to an x-ray tube housing).

A primary radiation diaphragm assembly such as this enables the beam of rays of the x-ray tube to be shaped to any optional image format. A so-called double-slot diaphragm has become known for this purpose, manifesting two pairs of plates which are adjustable in virtually one plane in mutually perpendicular directions, whereby the two plates of each pair are adjustable by means of an endless cable guided over cable pulleys disposed in mutual coaxial relation. Due to the finite extension of the focal point of the x-ray tube, a double slot diaphragm assembly such as this has the disadvantage that a penumbral region results about the actual shadow image which can be troublesome in certain instances.

With the aim of possibly avoiding this penumbra region, a so-called multi-depth diaphragm has been produced, such as is essentially the subject of the present invention, wherein a plurality of diaphragm planes are arranged in parallel and spaced apart from one another, and wherein the plates in the diaphragm planes are commonly adjustable in proportion to one another. As a consequence of the greater distance of the foremost diaphragm plane from the tube focal point (and thus a greater proximity to the patient), a shadow image is obtained having a considerably greater marginal definition. However, these multi-depth diaphragms have a rather complicated construction, and their manufacture therefore involves considerable outlay and expense.

A multi-depth diaphragm such as this is known which is assembled in building-block fashion from double-slot diaphragms adjustable by means of cable lines. The double slot diaphragms are coupled to one another by means of a suitable transmission gearing proportioned to the different distances of the diaphragm planes from the tube focal point. The disadvantage of this known x-ray primary ray diaphragm lies in its complicated construction, and, in addition, on account of the cable gearing, in its susceptibility to failure.

SUMMARY OF THE INVENTION

The object which is the basis of the invention consists in producing an x-ray primary ray diaphragm assembly of the type initially cited which is light, simple in construction, and reliably immune to malfunction or breakdown.

In accordance with the invention, this object is achieved by virtue of the fact that each close-to-focus diaphragm plate and the diaphragm plate remote-from-focus parallel thereto and opposite said first plate with regard to the diaphragm longitudinal axis, is secured to at least one lever, respectively, which lever is pivotably mounted about an axis lying between its diaphragm plates and parallel thereto, said axis being common to all four parallel diaphragm plates, so that the levers positioned on a common axis are capable of being swung in a scissors-like fashion, and that the length of the lever arms is selected to correspond to the desired position of the vertex of the pyramidal beam shape defined thereby. Due to the fact that pivotally mounted levers are used for supporting and adjusting the diaphragm plates, the diaphragm is simple in construction and reliable in operation.

Other objects, features and advantages of the present invention will be apparent from the following detailed description taken in connection with the accompanying sheets of drawings.

DETAILED DESCRIPTION

Figure 1:
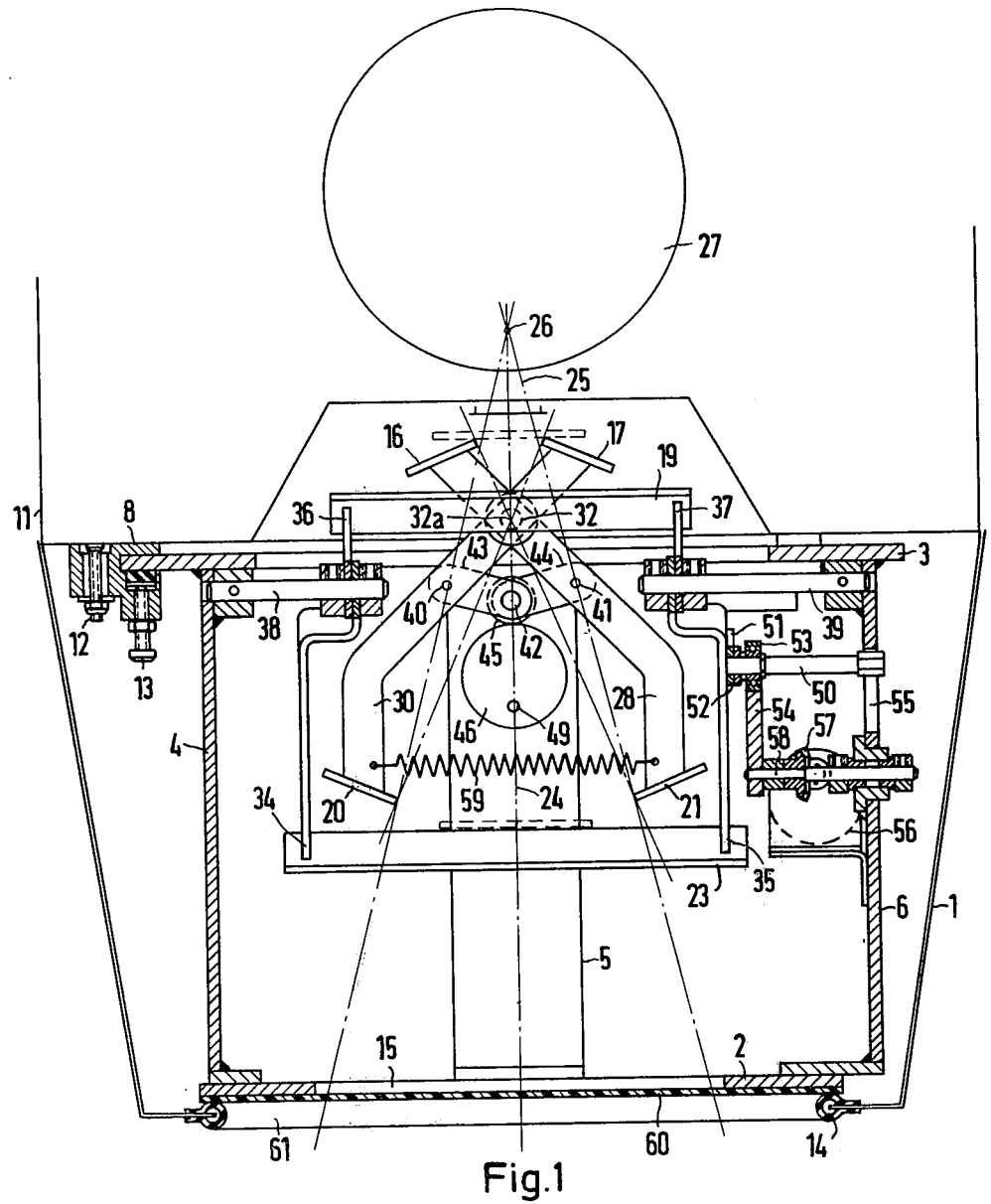
FIG. 1 illustrates a longitudinal sectional view of a primary x-ray diaphragm assembly in accordance with the present invention.
Figure 2:
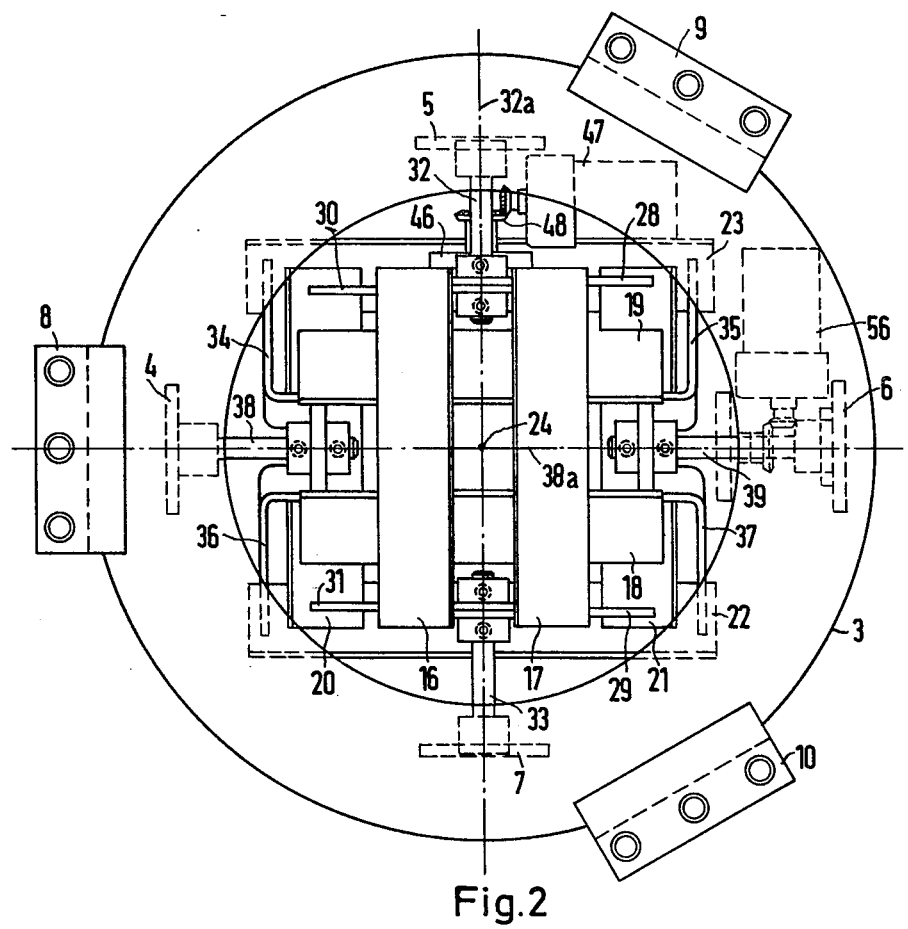
FIG. 2 shows a plan view of the primary x-ray diaphragm assembly of FIG. 1 detached from the housing of the x-ray tube.

FIGS. 1 and 2 illustrate an x-ray primary ray diaphragm assembly arranged in a diaphragm housing 1. The primary ray diaphragm assembly has a base plate 2, an opposite upper plate 3 and four supports 4 through 7 (FIG. 2) arranged at the periphery of plates 2, 3, and connecting said plates 2, 3. The framework 2 through 7 is secured to an x-ray tube housing 11, FIG. 1, by retaining plates 8, 9 and 10 (FIG. 2), provided on upper plate 3, by bolts, of which bolts 12 and 13 are illustrated in FIG. 1, serving to fasten the plates 8, 9, 10 to the housing 11. Base plate 2 and an x-ray-transmissive plate 60, FIG. 1, mounted beneath base plate 2, rest on a seal 14 enclosing the lower opening 61 of diaphragm housing 1. Base plate 2 exhibits an opening 15 opposite opening 61 of diaphragm housing 1. Plate 60 is composed of synthetic plastic material and acts as a closure for diaphragm housing 1.

In addition, the primary x-ray diaphragm assembly has two close-to-focus pairs of diaphragm plates 16, 17, and 18, 19 (FIG. 2), staggered 90°, and two remote-from-focus pairs of diaphragm plates 20, 21, and 22, 23, likewise staggered 90°. The plates of each pair of diaphragm plates, 16, 17; 18, 19; 20, 21; and 22, 23, are commonly adjustable in symmetry with the longitudinal axis 24 of the diaphragm assembly such that the diaphragmed pyramidal beam configuration 25 will have its vertex lying at the focus 26 of the x-ray tube 27. Each close-to-focus diaphragm plate, 16 through 19 (FIG. 2), and the respective parallel remote-from-focus diaphragm plate 20 through 23, oppositely positioned in relation to the longitudinal axis 24 of the diaphragm assembly, are mounted on levers which are pivotably mounted about an axis lying between such diaphragm plates and parallel thereto, said axis being common to all four parallel diaphragm plates. For each set of four parallel diaphragm plates, two levers are provided which are secured to the opposite ends of the diaphragm plates as shown in FIG. 2. Thus, the set of four diaphragm plates 16, 21 and 17, 20, (FIG. 2), are connected to one another by means of levers 28, 29 and 30, 31 and are swingable in a scissors-like fashion about the lever pivot arbors 32, 33 (FIG. 2), which lie on a common axis 32a. The outer ends of arbors 32, 33 are rigidly connected to supports 5 and 7, (FIG. 2). The four additional diaphragm plates 18, 23, and 19, 22 (FIG. 2), which are staggered 90° relative to diaphragm plates 16, 17, 20, 21, are connected to one another by means of levers 34, 35, and 36, 37 and are swingable in a scissors-like fashion about lever pivot arbors 38, 39 (FIG. 2), whose outer ends are secured to supports 4, 6 (FIG. 1). Here also, arbors 38, 39 lie on a common axis 38a (FIG. 2). The length of the lever arms is proportioned according to the distance of focus 26 from lever axes 32a, 38a, and is selected so that the position of the vertex of pyramidal configuration 25 defined by the diaphragm assembly coincides with such focus.

Mounted on the two levers 28, 30, connected in scissors-like fashion, there are two arms 43, 44 (FIG. 1) symmetrically linked to said levers by pivot pins 40, 41, and interconnected in an articulated fashion at pivot pin 42. In order to adjust diaphragm plates 16, 17, and 20, 21, a roller 45 is arranged on pivot pin 42, which roller rides on a cam plate or disc 46 and which is pressed against said cam disc in a resilient fashion. Tensioning of levers 28, 30 is effected by means of a tension spring 59 connected between them. In order to drive the cam disc 46, an electric motor 47 (FIG. 2) is provided which drives cam disc 46 via bevel gearing 48 (FIG. 2) and a shaft 49 (FIG. 1). In the position of cam disk 46 illustrated in FIGS. 1 and 2, the pairs of diaphragm plates 16 and 17, and 20 and 21 respectively, have been brought into the extreme position; i.e., the diaphragm is completely open. When cam disc 46 is turned (or rotated) by means of electric motor 47, the pairs of diaphragm plates 16 and 17, and 20 and 21, respectively, move toward one another until the desired position has been reached. When electric motor 47 is switched on in order to adjust the pairs of diaphragm plates 16, 17, and 20, 21, levers 29, 31 (FIG. 2) follow freely.

The two levers 35, 37 (FIG. 2), connected in scissors-like fashion for movement of the additional pairs of diaphragm plates 18, 19, and 22, 23, also have two arms 51, 52 (FIG. 1) linked symmetrically to said levers and interconnected at pivot pin 50 (FIG. 1) in an articulated fashion. In order to adjust the pairs of diaphragm plates 18, 19, and 22, 23, a roller 53 also serves this purpose here, said roller riding on a cam disc 54 and being pressed against the latter in a resilient fashion. Tensioning of levers 35, 37 is effected by means of a non-illustrated tension spring connected between them in the same way as spring 59 (FIG. 1) is connected between levers 28, 30. FIG. 1 illustrates that the free end of pivot pin 50 runs in a slot 55 proceeding in a longitudinal direction in support 6, in order that roller 53 is enabled to move only in the direction of axis 24. The same applies to pivot pin 42. Here, the corresponding slot is arranged in support 5. In order to drive cam disc 54, an electric motor 56 (FIG. 2) is provided which drives the cam disc 54 via bevel gearing 57 and a shaft 58. The control of movement of the pairs of diaphragm plates 18, 19 and 22, 23, proceeds in the same manner as described previously in connection with the pairs of diaphragm plates 16, 17, and 20, 21.

The length of the lever arms of levers 28 to 31, 34 to 37, calculated from the respective axis 32a, 38a, is proportioned such that the vertex of the pyramid configuration 25 defined by the diaphragm assembly coincides with the focus 26 in every position of diaphragm plates 16 through 23.

In the sample embodiment illustrated, for each set of four parallel diaphragm plates; namely, diaphragm plates 16, 17, 20, 21, and diaphragm plates 18, 19, 22, 23, two pairs of scissor levers are provided in each instance, said pairs of scissor levers consisting of levers 28 through 31, and 34 through 37, with the result that a particularly stable support mounting of all diaphragm plates 16 through 23 is ensured.

SUMMARY OF OPERATION

With the diaphragm assembly secured to housing 11 of the x-ray tube 27 as shown in FIG. 1, the four-sided pyramidal configuration 25 defined by the sets of diaphragm plates 16, 17, 20, 21, FIG. 1; and 18, 19, 22, 23, FIG. 2, converge at a vertex which coincides with the focus 26, FIG. 1, of x-ray tube 27. To adjust the angle of divergence of the x-ray beam as it is emitted from the diaphragm assembly via window 60, FIG. 1, the set of plates 16, 17, 20, 21 is moved inwardly from the extreme open position shown in FIG. 1 by energization of the motor 47 shown at the upper right in FIG. 2. Energization of motor 42 rotates cam 46, FIG. 1, via bevel gearing 48, FIG. 2, and shaft 49, FIG. 1, to allow tension spring 59 to progressively draw the levers 28, 30 toward each other. Similarly, with respect to the other plane (at right angles to the plane of FIG. 1 and coinciding with the axis 32a in FIG. 2), motor 56 (shown at the right in FIG. 2) is energized to rotate cam 54 shown at the right center in FIG. 1, allowing the roller 53 with its shaft 50 to move downwardly, the right hand end of shaft 50 riding in the vertical slot 55 shown at the extreme right center of FIG. 1. A tension spring (not shown) corresponding to tension spring 59, FIG. 1, is connected between levers 35 and 37, FIG. 2, so as to progressively move the plates 18, 19 and 22, 23 toward each other as the cam 54 rotates from the position illustrated in FIG. 1 (which corresponds to the position of cam 46 shown in FIG. 1). During the progressive closure of the diaphragm plates, the pyramidal configuration 25 defined by the plates continues to have its vertex coincide with the focus 26 of x-ray tube 27.

It will be apparent that many modifications and variations may be effected without departing from the scope of the novel teachings and concepts of the present invention.

We claim as our invention:

1. A primary x-ray diaphragm assembly comprising two pairs of diaphragm plates, staggered 90°, for mounting in operative relation to an x-ray tube in a relatively close-to-focus position, and further comprising two pairs of diaphragm plates, likewise staggered 90°, for mounting in a relatively remote-from-focus position, the plates of each pair of diaphragm plates being commonly adjustable symmetrically to the longitudinal axis of the diaphragm assembly such that, in the mounted state, the diaphragmed pyramid configuration defined thereby has its vertex lying substantially at the focus of the x-ray tube, characterized in that each close-to-focus diaphragm plate and a complementary remote-from-focus diaphragm plate oppositely disposed with reference to the diaphragm longitudinal axis are secured to at least one lever, respectively, which is pivotably mounted about an axis lying between such diaphragm plates, said axis being common to four diaphragm plates, with the levers pivotal on a common axis being capable of being pivoted in a scissors-like fashion, and with the length of the lever arms being selected to correspond to the desired position of the vertex of the pyramid configuration defined by said diaphragm plates, and characterized in that, on two levers, connected in scissors-like fashion, two arms are provided for each lever axis, said arms being symmetrically linked to said levers and being interconnected in an articulated fashion.

2. A diaphragm assembly according to claim 1, characterized in that, in order to adjust the diaphragm plates a roller is arranged at that location where the arms are interconnected, said roller running on a cam disc and being pressed against the latter in a resilient fashion.

3. A diaphragm assembly according to claim 2, characterized in that electric motors are provided for driving the cam discs.

* * * * *